United States Patent
Ramhold et al.

(10) Patent No.: US 8,205,353 B2
(45) Date of Patent: Jun. 26, 2012

(54) VACUUM CONCENTRATOR AND METHOD FOR VACUUM CONCENTRATION

(75) Inventors: Frank Ramhold, Freyburg (DE); Klaas Van Den Berghe, Hekelgem (BE); Bert-Olaf Grimm, Leipzig (DE); Wolfgang Goemann, Hamburg (DE); Rebecca Hess, Hamburg (DE); Felix Francke, Hamburg (DE)

(73) Assignee: Eppendorf AG, Hamburg (DE)

( * ) Notice: Subject to any disclaimer, the term of this patent is extended or adjusted under 35 U.S.C. 154(b) by 1096 days.

(21) Appl. No.: 11/927,949

(22) Filed: Oct. 30, 2007

(65) Prior Publication Data

US 2008/0115382 A1    May 22, 2008

(30) Foreign Application Priority Data

Nov. 18, 2006 (DE) .................. 10 2006 054 481

(51) Int. Cl.
*F26B 13/30* (2006.01)

(52) U.S. Cl. .................. 34/92; 34/202; 34/242; 422/72; 73/865; 159/6.1

(58) Field of Classification Search .................. 34/381, 34/407, 4, 20, 524, 90, 201, 242; 422/72; 73/865; 159/6.1
See application file for complete search history.

(56) References Cited

U.S. PATENT DOCUMENTS

| | | | | |
|---|---|---|---|---|
| 5,368,171 A | * | 11/1994 | Jackson | .................. 134/147 |
| 6,605,474 B1 | * | 8/2003 | Cole | .................. 436/177 |
| 6,722,214 B1 | | 4/2004 | Cole | |
| 6,878,342 B2 | | 4/2005 | Cole | |
| 2004/0071595 A1 | * | 4/2004 | Neeper et al. | .................. 422/72 |
| 2008/0115382 A1 | * | 5/2008 | Ramhold et al. | .................. 34/406 |

FOREIGN PATENT DOCUMENTS

| | | |
|---|---|---|
| CH | 681279 A5 | 2/1993 |
| DE | 34 13 385 A1 | 10/1985 |
| DE | 35 29 956 A1 | 2/1987 |
| DE | 36 18 436 A1 | 3/1987 |
| DE | 195 18 540 A1 | 11/1996 |
| DE | 699 18 734 T2 | 4/2005 |
| EP | 0 818 223 A1 | 9/1997 |
| JP | 2002504413 | 2/2002 |
| JP | 2005140536 | 6/2005 |
| JP | 2006504518 | 2/2006 |
| JP | 2008126228 A * | 6/2008 |
| WO | 0140763 A1 | 6/2001 |

* cited by examiner

*Primary Examiner* — Stephen M. Gravini
(74) *Attorney, Agent, or Firm* — Vidas, Arrett & Steinkraus, P.A.

(57) ABSTRACT

Vacuum concentrator, comprising a vacuum chamber with a closure which may be sealed in an airtight manner, a centrifuge rotor arranged in the vacuum chamber with at least one receiver for at least one vessel for samples to be dried, a drive motor arranged outside the vacuum chamber for driving the centrifuge rotor, a vacuum pump connected to the vacuum chamber, a tempering device associated with the vacuum chamber for tempering the at least one sample in the vacuum chamber, a pressure sensor associated with the vacuum chamber for detecting the pressure inside the vacuum chamber and an electrical control and evaluating device which is connected to the drive motor, the vacuum pump, the tempering device and the pressure sensor, for detecting the end point of the vacuum concentration by means of the pressures detected by the pressure sensor in the vacuum chamber and terminating the vacuum concentration when the end point is determined.

10 Claims, 5 Drawing Sheets

VACUUM CONCENTRATOR AND METHOD FOR VACUUM CONCENTRATION

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The invention relates to a vacuum concentrator and to a method for vacuum concentration.

Vacuum concentration is used in the chemical industry and in the laboratory, in particular within the scope of solid-liquid extraction and for drying wet, thermally unstable samples. In this connection, the fact that the boiling point of a liquid is reduced in the vacuum is utilized. As a result, the boiling liquid in the vacuum may escape from a wet sample at relatively low temperatures. To this end, the samples are arranged in a vacuum chamber which is evacuated by means of a vacuum pump. In order to prevent an uncontrolled release of liquid from the samples, said samples are arranged in the vacuum chamber in a centrifuge rotor. The heat for the vaporization is generated by means of electrical or other heating devices. The released liquid vapour is pumped off by the vacuum pump. A condenser optionally arranged between the vacuum chamber and the vacuum pump and/or a cryogenic trap arranged there, is able to capture the liquid vapour upstream of the vacuum pump, so that the vacuum pump produces a particularly strong vacuum and the drying performance is particularly efficient.

The end point of the vacuum concentration is the point in time at which the sample is dry and/or no more vaporized liquid leaves the sample. Known vacuum concentrators operate with centrifugation times which are too long in order to ensure that the liquid has completely left the sample. However, there is the risk that the samples have not been dried for long enough, so that considerable portions of residual liquid remain in the samples. It is further known to switch on the heating of the samples at the end of the concentration process once again, in order to vaporize the residual fluid by intense heating of the samples. Subsequent heating of samples which are already completely dried may lead to overheating of the samples.

Radiation heat or microwaves are used, in particular, for heating the samples as heat transmission by conduction is greatly reduced in a vacuum. Overheating of the multiple temperature-sensitive samples has to be avoided. According to DE 699 18 734 T2, the entire contents of which is incorporated herein by reference, the temperature of the vaporizing liquid samples in the vacuum concentrator is determined by the pressure during the vaporizing process being detected, an electrical pressure-data signal being generated in proportion with the sampled pressure, the pressure-data signal being transmitted to an electronic data signal processing unit, which has access to data about the volatile components present in the samples, in order to convert the pressure-data signal into a temperature value, which corresponds to the vapour pressure for the known volatile component and/or the known volatile components of the sample. In this connection, it is disadvantageous that an indication of the liquid and/or the solvent is required and the data have to be present for the relevant solvent.

Proceeding therefrom, the object of the invention is to provide an effective device and an effective method for vacuum concentration.

BRIEF SUMMARY OF THE INVENTION

The vacuum concentrator according to the invention comprises a vacuum chamber with a closure which may be sealed in an airtight manner, a centrifuge rotor arranged in the vacuum chamber with at least one receiver for at least one vessel for samples to be dried, a drive motor arranged outside the vacuum chamber for driving the centrifuge rotor, a vacuum pump connected to the vacuum chamber, a tempering device associated with the vacuum chamber for tempering the at least one sample in the vacuum chamber, a pressure sensor associated with the vacuum chamber for detecting the pressure inside the vacuum chamber and an electrical control and evaluating device which is connected to the drive motor, the vacuum pump, the tempering device and the pressure sensor, for detecting the end point of the vacuum concentration by means of the pressures detected by the pressure sensor in the vacuum chamber and terminating the vacuum concentration when the end point is determined.

In the method according to the invention for the vacuum concentration of samples, at least one vessel with a sample to be dried is arranged in a centrifuge rotor in a vacuum chamber and the vacuum chamber is sealed in an air-tight manner, the centrifuge rotor is rotated, the vacuum chamber is evacuated, the at least one sample is tempered in the vacuum chamber, the pressure prevailing in the vacuum chamber is detected, by means of the detected pressure, it is detected when the end point of the vacuum concentration is reached and the vacuum concentration is terminated when the end point is reached.

During the vacuum concentration, the pressure in the vacuum chamber is determined by the mass fluxes of the pumped off gases and/or vapours, of the air possibly flowing in as a result of leakages and the liquid vaporizing from the samples. At the end point of the drying, the last-mentioned effect is eliminated, as sample liquid is no longer vaporized. This time point may be established by monitoring the pressure inside the vacuum chamber. The invention is based on the fact that it detects the end point of the vacuum concentration by means of the detected pressure in the vacuum chamber and the vacuum concentration is terminated when the end point is determined. As a result, it is possible to carry out the vacuum concentration completely automatically. Prior knowledge of the material composition and/or the material data of the liquid to be vaporized and/or the solvent to be vaporized is not required. Thermal damage to the samples by overheating of the completely dried samples is avoided. Moreover, the duration of the vacuum concentration is shortened. The efficiency of the vacuum concentration is improved. Technically, the invention may additionally be easily implemented, as in principle it only requires the installation of a pressure sensor and a correspondingly designed control and evaluating device. The control and evaluating device may, in particular, be correspondingly configured hardware or a software-controlled data processing device.

The detection of the end point of the vacuum concentration by means of the measured pressures in the vacuum chamber may be carried out in different ways. According to one embodiment, the detected pressures are compared with at least one given value and, when reaching the at least one given value, the vacuum concentration is terminated. For example, a given value corresponds to the minimum pressure (end pressure) which may be achieved in a specific vacuum chamber where leakages are possibly present, by using a specific vacuum pump after vaporizing all the moisture from the samples. A plurality of given values may, for example, be predetermined, in order to take into account that the end pressure is gradually approached over lengthy evacuation times. As a result, relatively short evacuation times indicate the measurement of relatively high pressure-given values and, with very long evacuation times, the measurement of the end pressure indicates that the end point of the vacuum concentration has been reached. Moreover, it is possible from the detected pressures and possibly further detected data, such as for example the time, to compare derived values with given values for said derived values, for example, the derivative of the pressure-time curve or the integral of the pressure-time curve or the pressure-time ratio.

According to a further embodiment, a vacuum pump with a relatively low delivery rate is applied to the vacuum chamber, which only gradually lowers the pressure in the vacuum chamber until the end point is reached, so that when the end point is reached, as a result of the absence of the release of vaporized sample components, the pressure in the vacuum chamber drops rapidly and the reaching of the end point is detected using the rapid pressure drop. The rapid pressure reduction may be particularly easily determined. This method allows the end point to be particularly reliably determined.

According to a further embodiment, (a) for the duration of a pumping phase the vacuum pump is switched on and/or the vacuum is applied to the vacuum chamber, (b) for the duration of a switch-off phase, the vacuum pump is switched off and/or the vacuum is disconnected from the vacuum chamber, (c) the pressures in the vacuum chamber are detected during the switch-off phase, (d) by means of the pressures detected in the switched-off phase, it is determined whether the end point of the vacuum concentration is reached and (e) when the end point is determined, the vacuum concentration is terminated or the steps (a) to (e) are repeated, in case the end point has not been reached.

The idea underlying this embodiment is that, as a result of the vaporizing liquid components of the sample, the pressure rises in the vacuum chamber, when the vacuum pump is switched off and/or the vacuum is disconnected from the vacuum chamber. Additionally to the flushing of the vacuum pump by means of fresh air, the switch-off phase is optionally used for forcing out liquid possibly collected therein. In a subsequent pumping phase, the vacuum pump has to pump out the liquid vaporized in the switch-off phase. With increased drying of the sample, the rise in pressure in the switch-off phase becomes even smaller, corresponding to the reduced vaporizing of liquid. As a result, in the subsequent pumping phase, the vacuum pump has to pump off a smaller amount. Accordingly, the detection of the end point by evaluating the pressure rise is able to take place in the switch-off phase. With a hermetically sealed vacuum chamber, the pressure increase indicates a further release of vapours from the samples. Possible leakages from the pressure chamber, for example, during a trial operation of the vacuum chamber without samples contained therein may be detected and deducted from the pressure rise in order to detect the component of the release of vaporized liquid with a rise in pressure. If the pressure no longer rises in the switch-off phase after deducting the rise as a result of leakages, the end point has been reached.

According to a further embodiment, the pressure is regulated in the vacuum chamber to a set value by detecting the pressure in the vacuum chamber by means of the pressure sensor and detecting the end point of the vacuum concentration by the evaluation of a control or command signal of the vacuum pump (for example a signal of a speed sensor or the current or the voltage of an electrical drive motor of the vacuum pump). If, with the hermetically sealed vacuum chamber, no liquid is vaporized, the vacuum pump is not actuated, whereby it is indicated that the end point has been reached. Possible leakages of the vacuum chamber may be detected in an experiment without samples. The control or command signal required thereby of the vacuum pump may be detected and deducted from the control or command signals when drying samples. Thus the portion of the control or command signals which is based on the further release of gases from the samples, may be detected. With the elimination thereof, the end point is reached.

The process of vacuum concentration may be cancelled in different ways. According to one embodiment, the vacuum concentration is terminated by switching off the drive motor and/or the vacuum pump and/or the tempering device and/or opening the closure of the vacuum chamber.

The samples are preferably tempered by radiation heat. For example, to this end, the walls of the vacuum chamber are heated. For maintaining constant drying conditions and/or for avoiding overheating of the samples, according to one embodiment the tempering device and a temperature sensor associated with the vacuum chamber are connected to the control and evaluating device for monitoring the temperature in the vacuum chamber and/or regulating the temperature in the vacuum chamber to a set value. The set value may possibly be set according to the sample to be dried.

The vacuum concentrator according to the invention comprises a vacuum chamber with a closure which may be sealed in an airtight manner, a centrifuge rotor arranged in the vacuum chamber with at least one receiver for at least one vessel for samples to be dried, a drive motor arranged outside the vacuum chamber for driving the centrifuge rotor, a vacuum pump connected to the vacuum chamber, a tempering device associated with the vacuum chamber for tempering the at least one sample in the vacuum chamber, a temperature sensor in a suction tube opening into the vacuum chamber and connected to the vacuum pump and an electrical control and evaluating device which is connected to the drive motor, the vacuum pump, the tempering device and the temperature sensor, for regulating the temperature of the samples to a set value.

The vacuum concentrator may advantageously comprise at least one of the further features of the aforementioned vacuum concentrators.

In the method according to the invention for vacuum concentration of samples, at least one vessel with a sample to be dried is arranged in a centrifuge rotor in a vacuum chamber and the vacuum chamber is sealed in an airtight manner, the centrifuge rotor is rotated, the vacuum chamber is evacuated, the at least one sample is tempered in the vacuum chamber, the temperature is detected in a suction tube for applying a vacuum to the vacuum chamber and by means of the detected temperature the temperature of the samples is regulated to a set value.

The method according to the invention may advantageously comprise at least one of the further features of the previously explained method.

As the temperature sensor is arranged in a suction tube opening into the vacuum chamber and connected to the vacuum pump, the temperature sensor comes into intimate contact with the released vapours. The suction tube screens the temperature sensor from the surrounding regions of the vacuum chamber, so that it is avoided that the measurement is effected by heat exchange of the temperature sensor with the walls of the vacuum chamber. As a result, a more accurate monitoring and/or regulation of the temperature of the sample is permitted and the efficiency of the vacuum concentration is improved.

According to a preferred embodiment, the suction tube is aligned with the centre of the centrifuge rotor. In the centre of the centrifuge rotor, the vapours released by the samples may be particularly easily suctioned, so that the temperature of the samples may be particularly easily measured, by means of the temperature sensor arranged in the suction tube.

The tempering device is preferably a heating device, in particular an electrical heating device. The heating device is, in particular, arranged and configured such that it heats at least one internal wall of the vacuum chamber. Preferably all internal walls of the vacuum chamber are uniformly heated.

BRIEF DESCRIPTION OF THE SEVERAL VIEWS OF THE DRAWINGS

The invention is described hereinafter with reference to the accompanying drawings of embodiments and diagrams, in which.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated.

Figure 1:
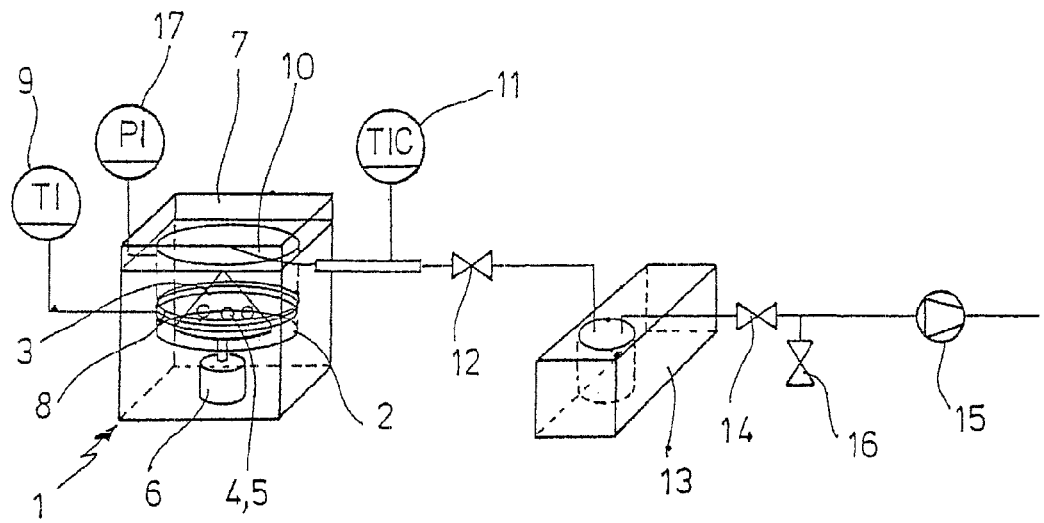
FIG. 1 shows a vacuum concentrator in an approximately schematic perspective view.

According to FIG. 1, the vacuum concentrator comprises a housing 1, with a vacuum chamber 2, in which a centrifuge rotor 3 is arranged with a plurality of receivers 4 for sample vessels 5. Outside the vacuum chamber 2 a drive unit 6 (for example with an electrical drive motor) for driving the centrifuge rotor 3 is arranged in the housing 1.

The vacuum chamber 2 is sealed at the top by a closure in the form of a sealing cover 7, which may be folded back.

A heating device 8 is associated with the vacuum chamber 2, and which comprises electrical resistance wires, which surround the vacuum chamber 2. A temperature sensor 9 for measuring the temperature of the heating device 8 is associated with the heating device 8, in order to avoid overheating of the heating device.

A suction tube 10 opens centrally above the centrifuge rotor 3, which is extended radially below and/or inside the cover 7. The opening of the suction tube 10 is axially aligned with the centrifuge rotor 3.

A further temperature sensor 11 is located in the suction tube 10.

Figure 2:
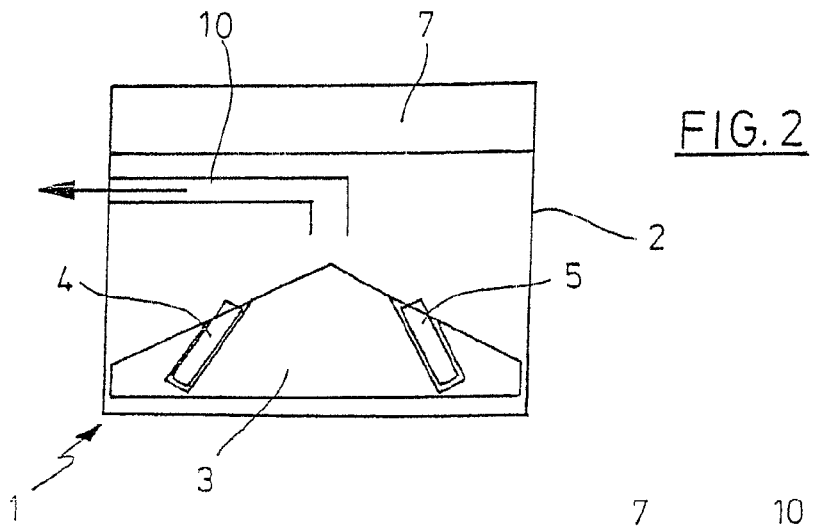
FIG. 2 shows the vacuum chamber of the vacuum concentrator with the suction tube below the cover in vertical section.

According to FIG. 2, the temperature sensor 11 is arranged in the suction tube 10 below the cover 7. The suction tube 10 is preferably foldable, pivotable or flexible, so that it may be removed for inserting and removing the centrifuge rotor 3 or vessels 5.

Figure 3:
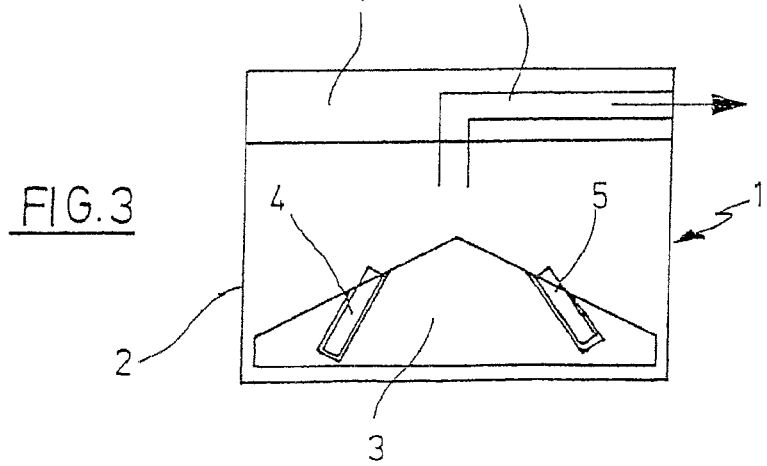
FIG. 3 shows the vacuum chamber of the vacuum concentrator with an alternative arrangement of the suction tube in the cover in vertical section.
Figure 4:
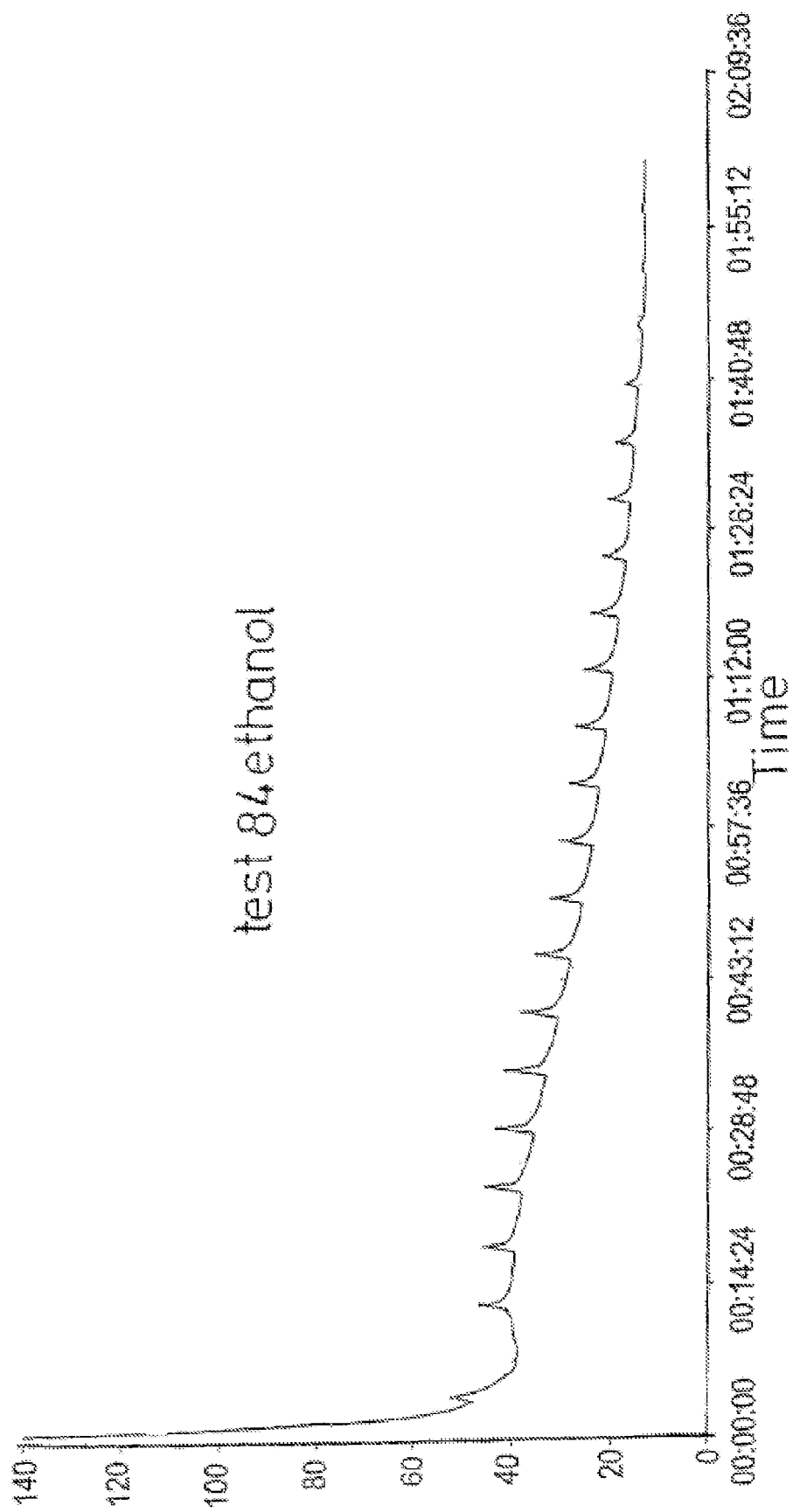
FIG. 4 shows the course of the pressure in the vacuum chamber over the time, during the vaporization of ethanol.

According to FIG. 3, the suction tube 10 is integrated in the cover 7 of the vacuum chamber 2. In both cases the suctioned vapour stream flows around the temperature sensor 11, so that excellent heat transmission values are also reached in the vacuum. The suction tube 10 protects against heat radiation, as due to the suctioned vapour on the inside of the suction tube 10 the same temperature is reached as on the temperature sensor 11 and thus no heat radiation is able to occur. Also, heat conduction from the walls of the vacuum chamber 2 to the suction tube 10 may be avoided by corresponding insulation of the suction tube 10 relative to the walls.

The suction tube 10 is connected via a valve 12 to a cryogenic trap 13. Said cryogenic trap is connected via a valve 14 to a vacuum pump 15. A further valve 16 is present upstream of the vacuum pump 15. The valves 12, 14, 16 may be electrically controlled.

Moreover, a pressure sensor 17 is connected to the vacuum chamber 1.

The drive motor 6, the heating device 8, the valves 12, 14, 16, the temperature sensors 9, 11, the vacuum pump 15 and pressure sensor 17 are electrically connected via electrical cables, not shown, to an electrical control and evaluating device 18.

When carrying out vacuum extraction, the centrifuge rotor 3 is rotated with the vessels 5 inserted. Moreover, by means of the further temperature sensor 11, the temperature of the samples in the vessels 5 is monitored and the heating device 8 regulated such that the samples inside the vessels 4 adopt a specific temperature. By means of the temperature sensor 9, possible overheating of the heating device 8 is intended to be detected.

The pump 15 is, moreover, operated such that when the valves 12, 14 are open and the valve 16 is closed, gases are sucked out of the vacuum chamber 2 through the suction tube 10. In the cryogenic trap 13 the suctioned vapours are condensed, so that the vacuum pump 15 has as large a throughput as possible, and as powerful a vacuum as possible is achieved in the vacuum chamber 2.

The pressure in the vacuum chamber 1 is continually detected via the pressure sensor 17.

As vapour is also condensed in the vacuum pump 15, again after the course of specific drying times, the valves 12, 14 are closed and the vacuum pump 15 switched off. Fresh air is conducted into the vacuum pump 15 via the valve 16, and, as a result, the moisture which is present is forced out of the vacuum pump 15. Subsequently, the valve 16 is closed, the vacuum pump 15 started again and the valves 12, 14 opened.

The pressure gradually reduces in the vacuum chamber 2. This is shown, for the example of a sample which contains ethanol as solvent, in FIG. 3. The spikes of the curve relate to the switch-off phases, in which pressure in the vacuum chamber rises again due to the further release of solvent and due to leakages.

In this example, a relatively low-powered vacuum pump 15 is used so that an end pressure in the order of approximately 15 mbar is only gradually achieved over the entire experiment time. This is the case when the height of the spikes in the switch-off phases is exceptionally low as hardly any solvent is vaporized.

It is thus possible to detect when the end point has been reached, by comparing the average pressure in the vacuum chamber 2 with the end pressure of the pump (approximately 15 mbar). In principle, the gradient of the pressure curve is also suitable for the detection of the end point. Moreover, the difference in the pressure in the vacuum chamber 2 at the start and at the end of the switch-off phases may be used, i.e. the height of the spikes.

The aforementioned control, monitoring, regulating and evaluation processes are controlled by the control and evaluating device 18.

Figure 5:
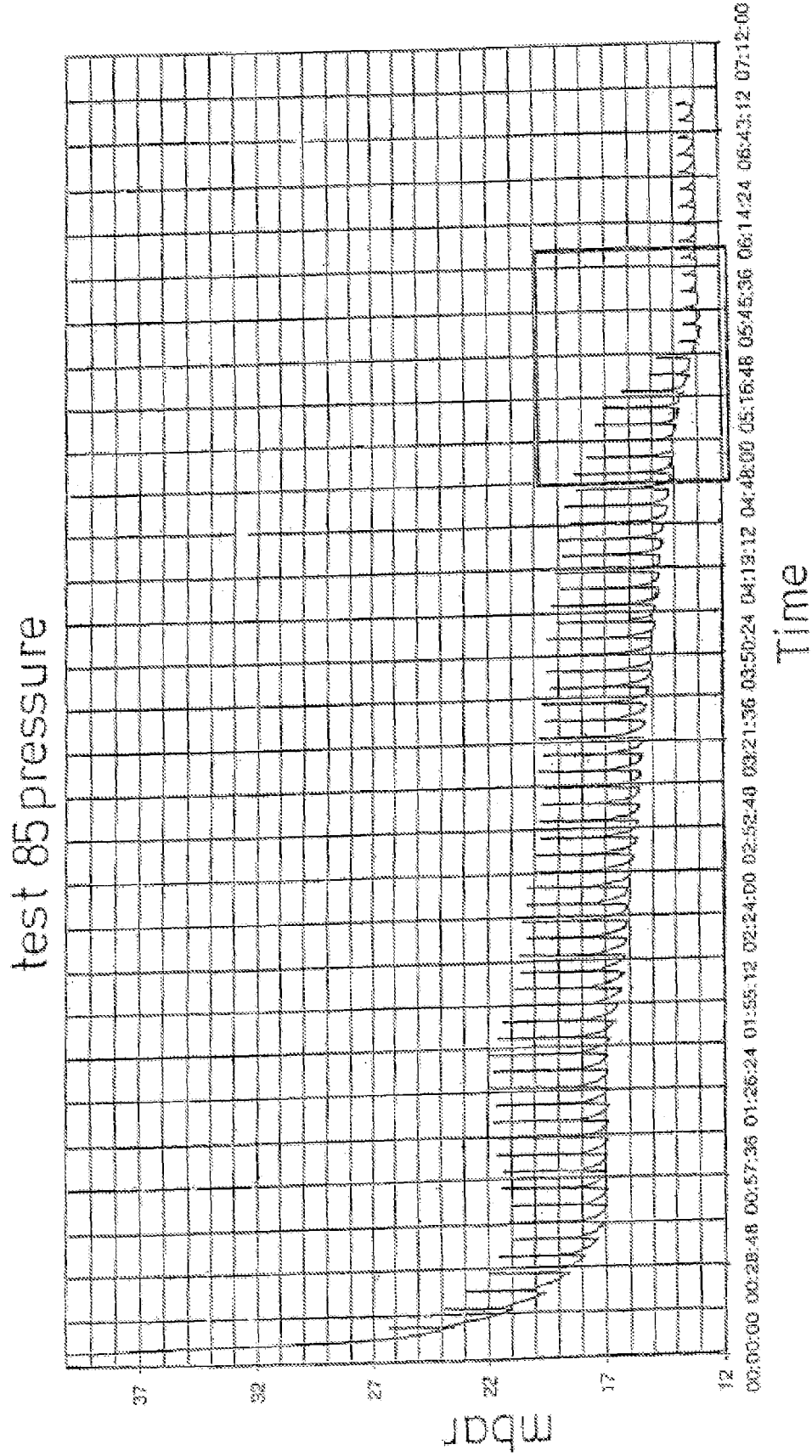
FIG. 5 shows the course of the pressure in the vacuum chamber over the time, for the vaporization of water.
Figure 6:
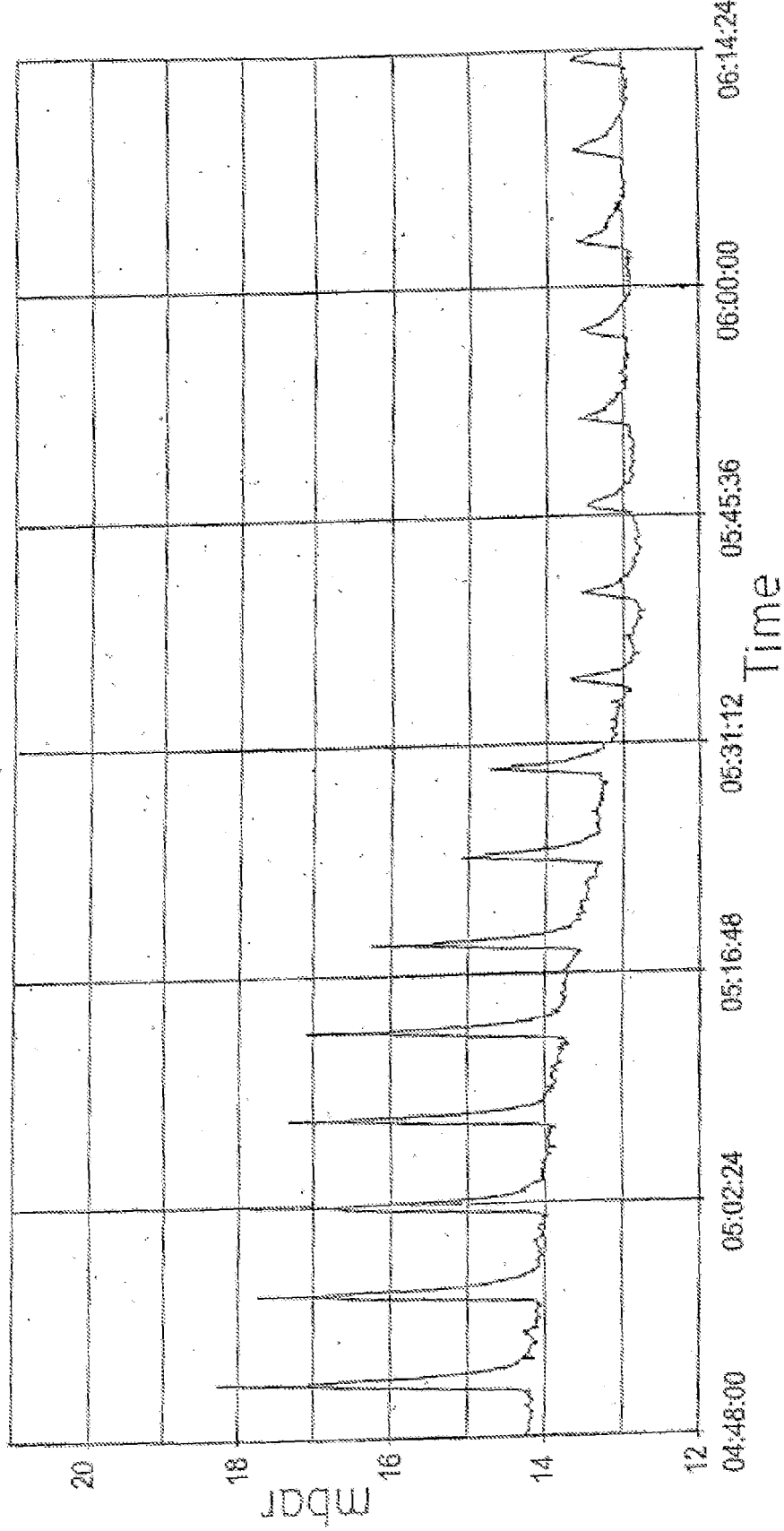
FIG. 6 shows an enlarged detail with the end point of FIG. 5.

FIGS. 5 and 6 demonstrate the pressure drop in the vacuum chamber 1 when using samples which contain water. The drying times are much longer than with ethanol, as water has a much lower vapour pressure than ethanol. The end pressure is, in turn, reached at the end point. Moreover, the gradient of the pressure curve markedly drops. Furthermore, the height of the spikes after reaching the end point is very low, as in the switch-off phases a pressure rise only takes place due to leakages.

Figure 7:
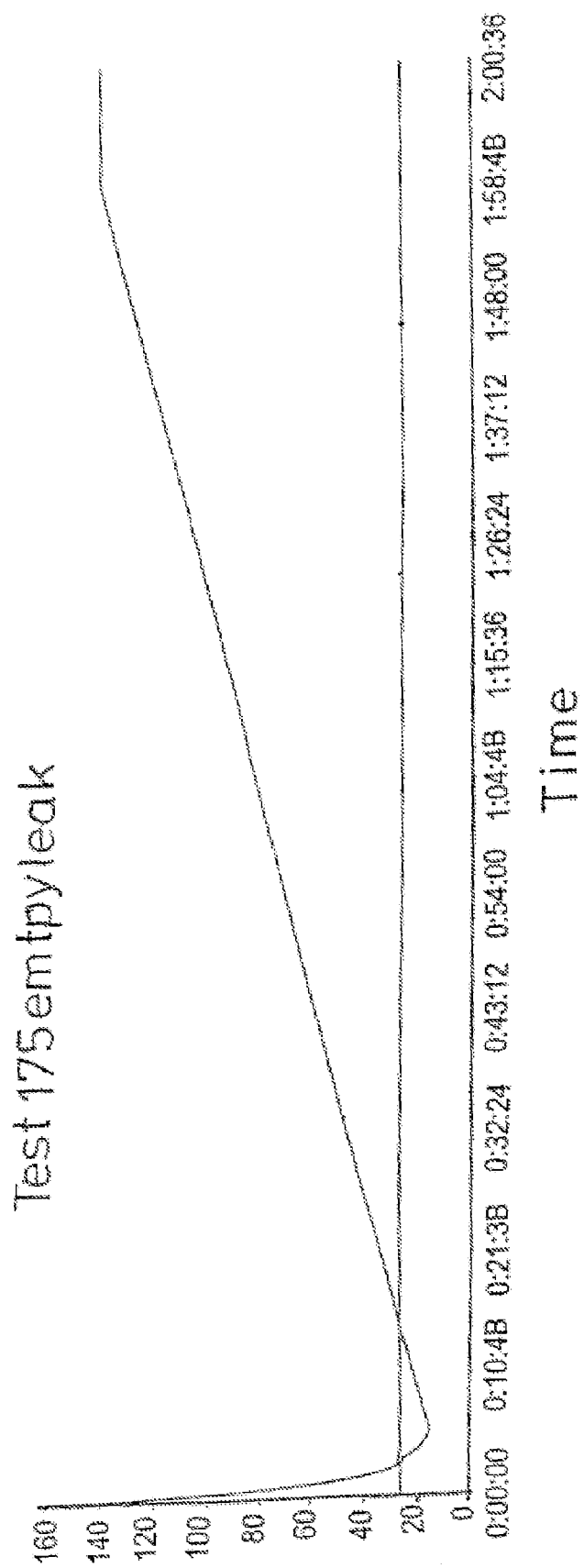
FIG. 7 shows the course of the pressure in the vacuum chamber without samples over the time, when stopping the vacuum pump after reaching the end point.

The leakage value of the system may be easily detected, by the vacuum concentrator being operated without samples and the vacuum pump 15 being stopped after reaching the end pressure. According to FIG. 7, the pressure gradually rises inside the vacuum chamber 1 due to the leakages. In a switch-off phase in which the course of the spikes corresponds to this leakage curve, the end point is reached.

Alternatively, with a variable speed vacuum pump 15 an internal pressure sensor of the vacuum pump 15 may be useful for detecting the controlled variable (pressure in the inlet of the vacuum pump). As soon as a control or command signal (for example a signal of a speed sensor or the current or the voltage of the electrical drive motor thereof) of the vacuum pump 15 drops, the end point of the centrifugation is reached as the vacuum pump 15 no longer delivers vapour from the vacuum chamber but air which enters as a result of leakages.

In principle, it is also possible to use a more powerful vacuum pump 15, in order to accelerate the drying. In the vacuum chamber 2, therefore, the end pressure is reached more rapidly than in the above examples. However, the end point of the centrifugation may be easily identified, for example by monitoring the height of the spikes in the switch-off phases.

A further possibility for identifying the end point is to detect the gradient of the pressure rise in the switch-off phases. This gradient drops sharply after reaching the end point, as no liquid sample components are then vaporized.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. Vacuum concentrator comprising a vacuum chamber (2) with a closure (7) which may be sealed in an airtight manner, a centrifuge rotor (3) arranged in the vacuum chamber (2) with at least one receiver (4) for at least one vessel (5) for samples to be dried, a drive motor (6) arranged outside the vacuum chamber (2) for driving the centrifuge rotor (3), a vacuum pump (15) connected to the vacuum chamber (2), a tempering device (8) associated with the vacuum chamber (2) for tempering the at least one sample in the vacuum chamber (2), a pressure sensor (17) associated with the vacuum chamber (2) for detecting the pressure inside the vacuum chamber (2) and an electrical control and evaluating device (18) which is connected to the drive motor (6), the vacuum pump (15), the tempering device (8) and the pressure sensor (17), for detecting the end point of the vacuum concentration by means of the pressures detected by the pressure sensor (17) in the vacuum chamber (2) and terminating the vacuum concentration when the end point is determined, wherein the vacuum pump (15) has a low delivery rate, which only gradually lowers the pressure in the vacuum chamber until the end point is reached, so that when the end point is reached, as a result of the absence of the release of vaporized sample components, the pressure in the vacuum chamber drops rapidly, and wherein the electrical control and evaluation device detects the reaching of the end point using the rapid pressure drop.

2. Vacuum concentrator according to claim 1 comprising a control and evaluating device (18) for detecting the end point of the vacuum concentration by comparing the detected pressure and/or the values derived therefrom with at least one given value and terminating the vacuum concentration when reaching the at least one given value.

3. Vacuum concentrator according to claim 1, comprising an evaluating and control device (18) for (a) switching on the vacuum pump (15) for the duration of a pumping phase, (b) switching off the vacuum pump (15) after the course of the pumping phase for the duration of a switch-off phase (c) detecting the pressures in the vacuum chamber (2) during the switch-off phase (d) determining, by means of the pressures detected in the switch-off phase, whether the end point of the vacuum concentration is reached and (e) terminating the vacuum concentration when the end point is determined or repeating the steps (a) to (e), if the end point has not been reached.

4. Vacuum concentrator according to claim 1 comprising a control and evaluating device (18) for regulating the pressure in the vacuum chamber (2) to a set value by detecting the pressure in the vacuum chamber (2) by means of the pressure sensor (17) and detecting the end point of the vacuum concentration by the evaluation of control or command signals of the vacuum pump (15).

5. Vacuum concentrator according to claim 1, comprising a control and evaluating device (18) for terminating the vacuum concentration by switching off the drive motor (6) and/or the vacuum pump (15) and/or the tempering device (8) and/or opening the closure (7).

6. Vacuum concentrator according to claim 1, in which the tempering device (8) and a temperature sensor (9) associated with the vacuum chamber (2), are connected to the control and evaluating device (18) for monitoring the temperature in the vacuum chamber (2) and/or regulating the temperature in the vacuum chamber (2) to a set value.

7. Vacuum concentrator comprising a vacuum chamber (2) with a closure (7) which may be sealed in an airtight manner, a centrifuge rotor (3) arranged in the vacuum chamber (2) with at least one receiver (4) for at least one vessel (5) for samples to be dried, a drive motor (6) arranged outside the vacuum chamber (2) for driving the centrifuge rotor (3), a vacuum pump (15) connected to the vacuum chamber (2), a tempering device (8) associated with the vacuum chamber (2) for tempering the at least one sample in the vacuum chamber (2), a temperature sensor (11) in a suction tube (10) opening into the vacuum chamber (2) and connected to the vacuum pump (15) and an electrical control and evaluating device (18) which is connected to the drive motor (6), the vacuum pump (15), the tempering device (8) and the temperature sensor (11), for regulating the temperature of the samples to a set value.

8. Vacuum concentrator according to claim 7, in which the suction tube (10) is aligned with the centre of the centrifuge rotor (3).

9. Vacuum concentrator comprising a vacuum chamber (2) with a closure (7) which may be sealed in an airtight manner, a centrifuge rotor (3) arranged in the vacuum chamber (2) with at least one receiver (4) for at least one vessel (5) for samples to be dried, a drive motor (6) arranged outside the vacuum chamber (2) for driving the centrifuge rotor (3), a vacuum pump (15) connected to the vacuum chamber (2), a tempering device (8) associated with the vacuum chamber (2) for tempering the at least one sample in the vacuum chamber (2), a pressure sensor (17) associated with the vacuum chamber (2) for detecting the pressure inside the vacuum chamber (2) and an electrical control and evaluating device (18) which is connected to the drive motor (6), the vacuum pump (15), the tempering device (8) and the pressure sensor (17), for detecting the end point of the vacuum concentration by means of the pressures detected by the pressure sensor (17) in the vacuum chamber (2) and terminating the vacuum concentration when the end point is determined, and further wherein the evaluating and control device (18) is for (a) switching on the vacuum pump (15) for the duration of a pumping phase, (b) switching off the vacuum pump (15) after the course of the pumping phase for the duration of a switch-off phase (c) detecting the pressures in the vacuum chamber (2) during the switch-off phase (d) determining, by means of the pressures detected in the switch-off phase, whether the end point of the vacuum concentration is reached and (e) terminating the vacuum concentration when the end point is determined or repeating the steps (a) to (e), if the end point has not been reached.

10. Vacuum concentrator comprising a vacuum chamber (2) with a closure (7) which may be sealed in an airtight manner, a centrifuge rotor (3) arranged in the vacuum chamber (2) with at least one receiver (4) for at least one vessel (5) for samples to be dried, a drive motor (6) arranged outside the vacuum chamber (2) for driving the centrifuge rotor (3), a vacuum pump (15) connected to the vacuum chamber (2), a tempering device (8) associated with the vacuum chamber (2) for tempering the at least one sample in the vacuum chamber (2), a pressure sensor (17) associated with the vacuum chamber (2) for detecting the pressure inside the vacuum chamber (2) and an electrical control and evaluating device (18) which is connected to the drive motor (6), the vacuum pump (15), the tempering device (8) and the pressure sensor (17), for detecting the end point of the vacuum concentration by means of the pressures detected by the pressure sensor (17) in the vacuum chamber (2) and terminating the vacuum concentration when the end point is determined, wherein the control and evaluating device (18) is for regulating the pressure in the vacuum chamber (2) to a set value by detecting the pressure in the vacuum chamber (2) by means of the pressure sensor (17) and detecting the end point of the vacuum concentration by the evaluation of control or command signals of the vacuum pump (15).

* * * * *